United States Patent

Oude Alink

[11] 4,346,223
[45] Aug. 24, 1982

[54] PREPARATION OF PERHYDROPHENANTHRIDINES

[75] Inventor: Bernardus A. Oude Alink, St. Louis, Mo.

[73] Assignee: Petrolite Corporation, St. Louis, Mo.

[21] Appl. No.: 264,900

[22] Filed: May 18, 1981

[51] Int. Cl.³ .................. C07D 221/20; C07D 221/12
[52] U.S. Cl. ...................................... 546/18; 252/401; 252/390
[58] Field of Search .......................................... 546/18

[56] References Cited

U.S. PATENT DOCUMENTS 4,012,392 3/1977 Akkerman ............................ 456/18

*Primary Examiner*—Robert T. Bond
*Attorney, Agent, or Firm*—Sidney B. Ring; Hyman F. Glass

[57] ABSTRACT

This invention relates to the reduction of THP to perhydrophenanthridines (PHA) with formic acid. This is illustrated by the following equation

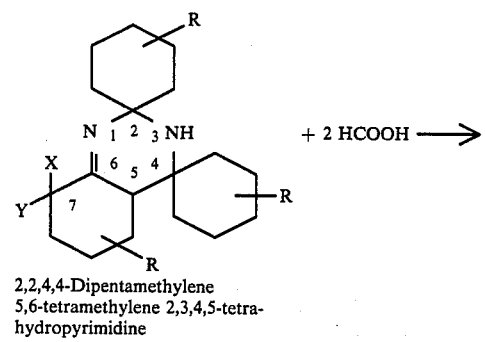

2,2,4,4-Dipentamethylene 5,6-tetramethylene 2,3,4,5-tetrahydropyrimidine

+ 2 HCOOH ⟶

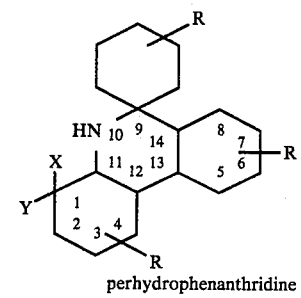

perhydrophenanthridine where R is hydrogen or a substituted group, such as hydrocarbon, for example alkyl, etc.; and X and Y are hydrogen or a substituted group, such as a hydrocarbon group containing a functional group, for example alkyl-X where X is a functional group such as nitrilo, carboxyl, etc. The perhydrophenanthridines of this invention are useful as corrosion inhibitors and as fuel stability additives.

12 Claims, No Drawings

PREPARATION OF PERHYDROPHENANTHRIDINES

In U.S. Pat. No. 4,085,104 there is described and claimed substituted 2,3,4,5-tetrahydropyrimidines (THP)

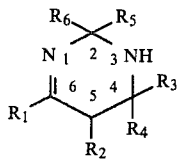

which are prepared by the following reactions:

(1) The reaction of a carbonyl compound (ketone or aldehyde) with ($NH_3$ or $NH_4OH$) and a sulfur-containing catalyst.

(2) The reaction of an $\alpha,\beta$-unsaturated ketone and a carbonyl compound and $NH_3$ (or $NH_4OH$) without a catalyst.

(3) Reaction of an $\alpha,\beta$-unsaturated ketone, a 1-aminoalcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula $(CH_2)_nC\!=\!O$ such as cyclohexanone, cyclopentanone, substituted derivatives thereof such as alkylcyclohexanone, dialkyl-cyclohexanone.

In U.S. Pat. No. 4,085,105 a class of compounds which are prepared by reducing THP and a unique method of preparing HHP which comprises using a formate salt such as ammonium formate. The use of ammonium formate is unique for the following reasons:

(1) In the preparation of THP from a carbonyl compound and ammonia, ammonium formate operates as a very efficient catalyst without being consumed.

(2) In the preparation of HHP from THP, ammonium formate serves as a reducing agent, yielding $CO_2$ and $NH_3$ as byproducts. It is often preferred to form ammonium formate by allowing ammonia to react with formic acid present during the initial phase of the reaction. The byproducts, produced in the process of preparing HHP from a carbonyl compound, formic acid and ammonia, are $H_2O$, $CO_2$, and $NH_3$ and are all easily removed.

The specific reaction in U.S. Pat. No. 4,085,105 is as follows:

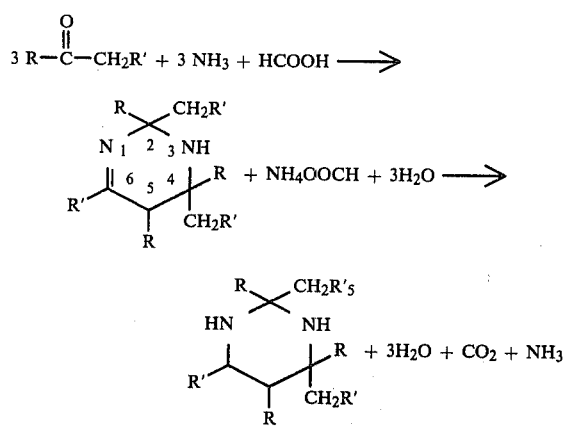

If a symmetric carbonyl compound is employed, i.e., $R\!=\!CH_2R'$ a single HHP will be produced, for example in the case of cyclohexanone, the reaction may be summarized as follows:

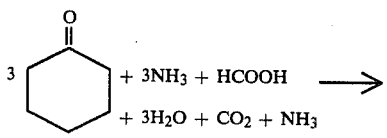

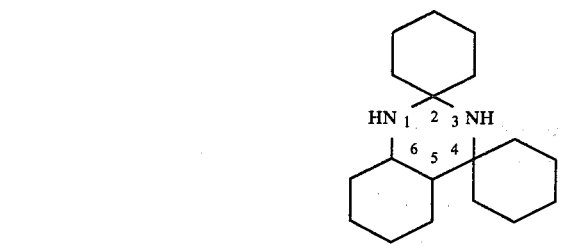

In the preferred method of U.S. Pat. No. 4,085,105, the carbonyl compound is reacted with ammonia in the presence of ammonium formate (or formic acid so as to form ammonium formate in situ) under pressure to keep the volatile components in the reaction mixture. The reaction is carried out at a temperature and time sufficient to produce THP, for example at a temperature of 20°-55° C. for preferably from 2-18 hrs.

In general the molar ratio of carbonyl to $NH_3$ to formic acid is at least 3 to 3 to 1 but preferably 3 to 3-4 to 1.

After completion of the formation of THP, the reaction mixture is further heated, preferably under reduced pressure to remove $H_2O$, $CO_2$ and $NH_3$ at a temperature of 40°-200° C. for 0.5 to 24 hrs. to produce HHP.

The preferred carbonyl compound is cyclohexanone. Not all carbonyl compounds can be used. For example methyl ethyl ketone (MEK) when reacted with ammonia in the presence of formic acid yields a mixture of 2,4,5,6-tetramethyl-2,4-diethyl) and 2,4-dimethyl-2,4,6-triethyl-2,3,4,5-tetrahydropyrimidine which upon further reaction with ammonium formate gives a mixture of dihydropyridines, a process involving deammoniation rather than reduction of the tetrahydropyrimidine moiety. However, MEK in combination with cyclohexanone yields the HHP.

Substituted cyclohexanones can also be used. Also mixtures of cyclohexanones and other ketones or aldehydes can be used so as to yield mixtures of substituted hexahydropyrimidines.

Thus, U.S. Pat. No. 4,085,105 reduces THP to HHP.

I have now discovered that THP can be reduced to perhydrophenanthridines (instead of the HHP of U.S. Pat. No. 4,085,105) by reacting THP with formic acid according to the following equation:

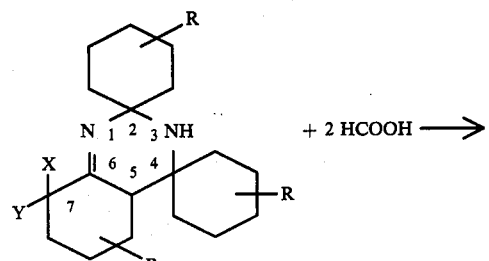

2,2,4,4-Dipentamethylene 5,6-tetramethylene 2,3,4,5-tetrahydropyrimidine

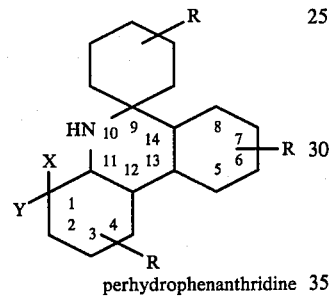

perhydrophenanthridine where R is hydrogen or a substituted group such as a hydrocarbon group, for example alkyl and X and Y are hydrogen or a substituted group such as a hydrocarbon group containing a functional group, for example an alkyl X group where X is a functional group such as nitrilo, carboxyl, etc.

The reaction is carried out by heating the THP with at lease 2 equivalents of formic acid but it may be desirable to use more than 2 equivalents such as 2-10 equivalents of formic acid. Reaction temperatures are from 60°-101° C. but a temperature of 101° C. (reflux) is preferred. Reaction times are from 1-24 hrs, such as 3-18 hrs, for example 6-16 hrs.

The products are useful as corrosion inhibitors and fuel stability additives.

EXAMPLE 1

2,2,4,4-Dipentamethylene-5,6-tetramethylene 2,3,4,5-tetrahydropyrimidine

A mixture of 294 grams of cyclohexanone and 5 grams of ammonium chloride was placed in a pressure reactor. Over a ¾ hour period 38.8 grams of ammonia gas was added. After the addition was complexed, the mixture was stirred for 5 hour at ambient temperature. The product was taken up in toluene and the aqueous phase which separated was discarded. The toluene solution was evaporated under diminished pressure to yield 268 grams of 2,2,4,4-dipentamethylene 5,6-tetramethylene 2,3,4,5-tetrahydropyrimidine, infrared spectrum 6.02μ (C=N) and 3.05μ (N—H), $C^{13}$ nuclear magnetic resonance spectrum, solvent CDCl$_3$, ref. TMS:

70.11(2), 50.16(4), 46.59(5), 169.38(6), 42.43(7), 29.30(8), 26.38(9), 29.30(10), 40.61(11), 21.90*(12), 26.38(13), 21.64*(14), 35.54(15), 38.53(16), 22.55*(17), 26.38(18), 22.55*(19), 38.53(20).

*values may be interchanged

EXAMPLE 2

9,13,18-Trimethyl 2,2,4,4-dipentamethylene-5,6-tetramethylene 2,3,4,5-tetrahydropyrimidine A mixture of 75 grams of 4-methylcyclohexanone, 6.1 grams of ammonium chloride and 300 grams of toluene were placed in a pressure reactor. To the mixture was added with stirring 16.2 grams of ammonia gas over a 15 minute period. After the addition was completed, the mixture was stirred for 20 hours. The aqueous layer was removed and the toluene layer evaporated under diminished pressure to yield 66 grams of 9,13,18-trimethyl 2,2,4,4-dipentamethylene 5,6-tetramethylene 2,3,4,5-tetrahydropyrimidine, infrared spectrum 6.01μ (N—H), $C^{13}$ nuclear magnetic resonance spectrum, solvent CDCl$_3$, reference T.M.S., δ in ppm.

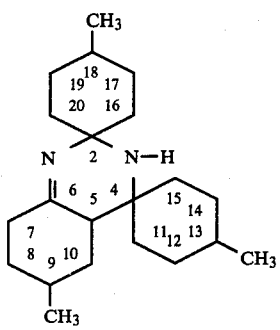

69.93(2), 49.67(4), 47.14(5), 169.60(6), 39.41(7), 34.67(8), 32.27(9), 34.67(10), 40.58(11), 29.80(12), 32.79(13), 29.80(14), 36.95(15), 37.85(16), 31.17(17), 32.79(18), 31.17(19), 37.85(20), 21.95(9-CH$_3$), 22.40(13-CH$_3$), 22.40(18-CH$_3$).

EXAMPLE 3

7-Propionitrile 2,2,4,4-Dipentamethylene 5,6-tetramethylene 2,3,4,5-tetrahydropyrimidine A mixture of 13.8 grams (0.05 M) of the product described in example 1 and 2.6 grams (0.05 M) of acrylonitrile were heated at 90° C. for 18 hours. Evaporation under diminished pressure yielded 16.2 grams of product. $^{13}$C nmr spectrum, solvent CDCl$_3$, ref. TMS, δ in ppm.

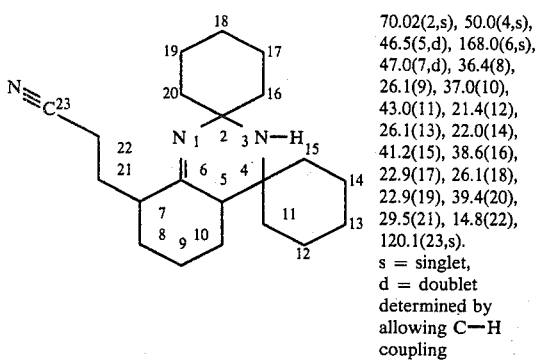

70.02(2,s), 50.0(4,s), 46.5(5,d), 168.0(6,s), 47.0(7,d), 36.4(8), 26.1(9), 37.0(10), 43.0(11), 21.4(12), 26.1(13), 22.0(14), 41.2(15), 38.6(16), 22.9(17), 26.1(18), 22.9(19), 39.4(20), 29.5(21), 14.8(22), 120.1(23,s).
s = singlet,
d = doublet determined by allowing C—H coupling

EXAMPLE 4

7-Dipropionitrile 2,2,4,4-Dipentamethylene 5,6-tetramethylene 2,3,4,5-tetrahydropyrimidine A mixture of 1.8 grams of the product described in example 1 (0.0066 M) and 6.5 grams (0.12 M) of acrylonitrile was refluxed for 19 hours. Evaporation under diminished pressure yielded dicyanoethylated 2,2,4,4-dipentamethylene 5,6-tetramethylene 2,3,4,5-tetrahydropyrimidine. $^{13}$C nmr, solvent CDCl$_3$, ref. TMS., δ in ppm:

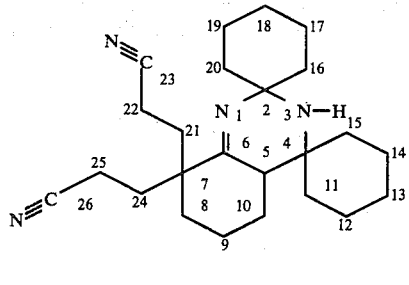

70.1(2,s), 50.4(4,s), 42.2(5,d), 166.7(6,s), 45.3(7,s), 33.9(8), 26.8(9), 35.6(10), 40.9(11), 20.5(12), 26.0(13), 21.2(14), 41.6(15), 40.5(16), 22.6(17), 26.0(18), 22.6(19), 38.4(20), 27.4(21), 12.1(22), 120.4(23,s), 31.3(24), 11.6(25), 119.6(26,s).
s = singlet, d = doublet determined by allowing C—H coupling

EXAMPLE 5

7-(Methylpropionate)-2,2,4,4-Dipentamethyl 5,6-tetramethylene 2,3,4,5-tetrahydropyrimidine A sample of 27.4 grams of the product described in example 1 and 8.6 grams of methylacrylate were heated for 18 hrs at 50° C. The resulting product was evaporated under diminished pressure to yield 35.9 grams of the substituted tetrahydropyrimidine: $^{13}$C nmr, solvent CDCl$_3$, ref. TMS, δ in ppm

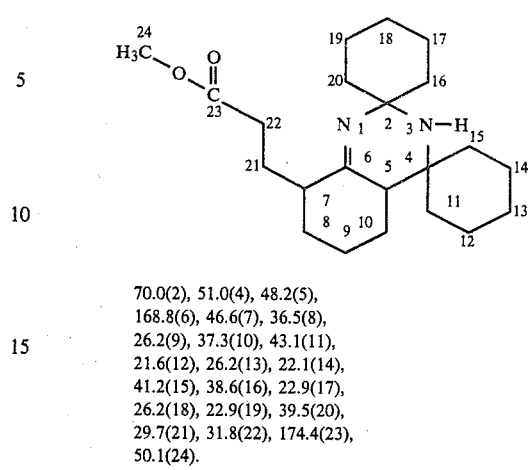

70.0(2), 51.0(4), 48.2(5), 168.8(6), 46.6(7), 36.5(8), 26.2(9), 37.3(10), 43.1(11), 21.6(12), 26.2(13), 22.1(14), 41.2(15), 38.6(16), 22.9(17), 26.2(18), 22.9(19), 39.5(20), 29.7(21), 31.8(22), 174.4(23), 50.1(24).

EXAMPLE 6

9,9-Pentamethylene perhydrophenanthridine

A mixture of 21.2 grams of 2,2,4,4-dipentamethylene 5,6-tetramethylene 2,3,4,5-tetrahydropyrimidine prepared as described in example 1 and 35 grams of formic acid were refluxed for 18 hours. The excess of formic acid was distilled off under diminished pressure and the resulting product basified with an aqueous sodium hydroxide solution. The product was extracted with ether and the ethereal solution washed with water. Removal of the ether yielded 20 grams of a crude product which was analyzed by ms/gc as a mixture of N-formylcyclohexylamine dicyclohexylamine and 9,9-pentamethylene perhydrophenanthridine. Separation by distillation yielded 9.2 grams of 9,9-pentamethylene perhydrophenanthridine. $^{13}$C nmr solvent CDCl$_3$, reference TMS, δ in ppm

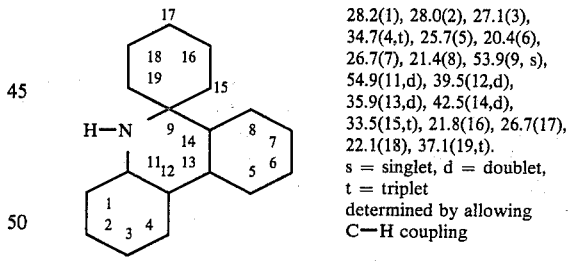

28.2(1), 28.0(2), 27.1(3), 34.7(4,t), 25.7(5), 20.4(6), 26.7(7), 21.4(8), 53.9(9, s), 54.9(11,d), 39.5(12,d), 35.9(13,d), 42.5(14,d), 33.5(15,t), 21.8(16), 26.7(17), 22.1(18), 37.1(19,t).
s = singlet, d = doublet, t = triplet determined by allowing C—H coupling As described in example 6, the perhydrophenanthridine listed in the Table below were prepared from the corresponding tetrahydropyrimidines.

TABLE

| Starting material | Example No. | Product |
|---|---|---|
| Product of example 2 | 7 | 3,7,17-Trimethyl,9,9-pentamethylene perhydrophenanthridine |
| Product of example 3 | 8 | 1-Propionitrile 9,9-pentamethylene perhydrophenanthridine |
| Product of example 4 | 9 | 1,1-Dipropionitrile 9,9-pentamethylene perhydrophenanthridine |

I claim:
1. A perhydrophenanthridine of the formula

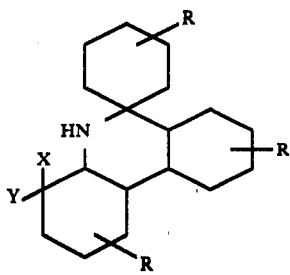

where R is hydrogen or a hydrocarbon and X and Y are hydrogen or a hydrocarbon group substituted with a functional group selected from the group consisting of carbonyl, carboxyl or nitrilo groups.

2. The composition of claim 1 where R is hydrogen or alkyl and X and Y are hydrogen.

3. The composition of claim 2 where R is hydrogen or methyl.

4. The composition of claim 1 where R is hydrogen or alkyl and where the functional group in X and Y are carbonyl, carboxyl, or nitrilo groups.

5. The composition of claim 4 where R is hydrogen or methyl.

6. The composition of claim 5 where X and Y are hydrogen, or alkylenenitrile, or alkylene ester groups.

7. A process of preparing the composition of claim 1 which comprises treating a tetrahydropyrimidine of the formula

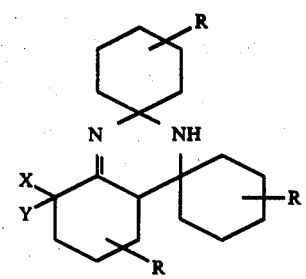

where R is hydrogen or a hydrocarbon group and X and Y are hydrogen or a hydrocarbon substituted with a functional group selected from the group consisting of carbonyl, carboxyl or nitrilo groups with formic acid.

8. A process for the composition of claim 2 which comprises treating a tetrahydropyrimidine of the formula

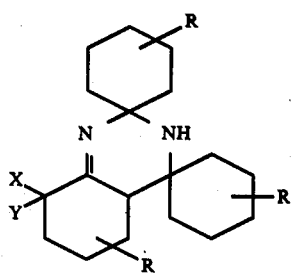

where R is hydrogen or alkyl and X and Y are hydrogen with formic acid.

9. A process of preparing the composition of claim 3 which comprises treating a tetrahydropyrimidine of the formula

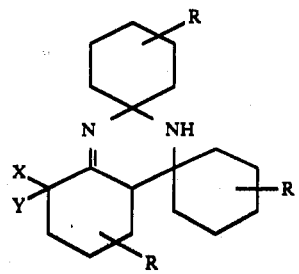

where R is hydrogen or methyl and X and Y are hydrogen with formic acid.

10. A process of preparing the composition of claim 4 which comprises treating a tetrahydropyrimidine of the formula

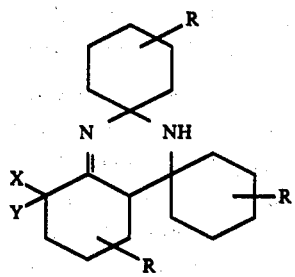

where R is hydrogen or alkyl and where the functional group in X and Y are carbonyl, carboxyl or nitrito groups with formic acid.

11. A process of preparing the composition of claim 5 which comprises treating a tetrahydropyrimidine of the formula

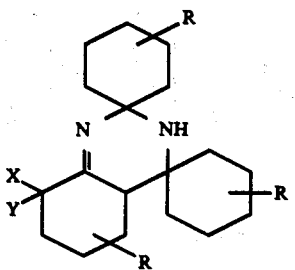

where R is hydrogen or methyl and where the functional group in X and Y are carbonyl, carboxyl or nitrito groups with formic acid.

12. A process of preparing the composition of claim 6 which comprises treating a tetrahydropyrimidine of the formula

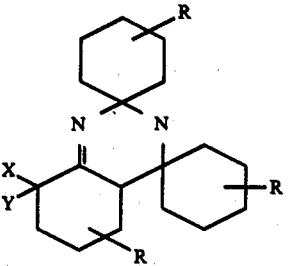

where R is hydrogen or methyl and the functional group in X and Y are hydrogen, alkylenenitrile, or alkylene ester groups with formic acid.

* * * * *